United States Patent
Wu et al.

(10) Patent No.: US 10,585,031 B2
(45) Date of Patent: Mar. 10, 2020

(54) LIGHT DETECTION SYSTEMS AND METHODS FOR USING THEREOF

(71) Applicant: Becton, Dickinson and Company, Franklin Lakes, NJ (US)

(72) Inventors: Austin Wu, San Jose, CA (US); David Thao Do, San Jose, CA (US); Timothy Wayne Petersen, Seattle, WA (US); Jianying Cao, San Jose, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 15/894,642

(22) Filed: Feb. 12, 2018

(65) Prior Publication Data
US 2018/0246029 A1  Aug. 30, 2018

Related U.S. Application Data

(60) Provisional application No. 62/464,282, filed on Feb. 27, 2017.

(51) Int. Cl.
| | |
|---|---|
| *G01N 15/14* | (2006.01) |
| *G01N 15/10* | (2006.01) |
| *G01N 21/05* | (2006.01) |
| *G01N 21/27* | (2006.01) |

(52) U.S. Cl.
CPC ....... *G01N 15/1436* (2013.01); *G01N 15/147* (2013.01); *G01N 15/1434* (2013.01); *G01N 21/05* (2013.01); *G01N 21/27* (2013.01); *G01N 2015/1006* (2013.01)

(58) Field of Classification Search
CPC .......... G01N 15/1434; G01N 15/1459; G01N 21/6486; G01N 21/645; G01N 2015/1006; G01N 2201/062; G01N 2201/068; G01N 2201/06113; G01N 2201/08
USPC ............ 356/72, 343, 339, 73, 419, 417, 442
See application file for complete search history.

(56) References Cited

U.S. PATENT DOCUMENTS

| | | | | |
|---|---|---|---|---|
| 4,690,561 A | * | 9/1987 | Ito | G01N 15/1434 250/201.1 |
| 5,408,307 A | * | 4/1995 | Yamamoto | G01N 15/1456 356/336 |
| 5,422,712 A | * | 6/1995 | Ogino | G01N 15/1434 250/458.1 |
| 5,684,575 A | * | 11/1997 | Steen | G01N 15/14 356/73 |
| 5,995,235 A | * | 11/1999 | Sui | G01N 21/255 356/419 |
| 6,198,864 B1 | | 3/2001 | Lemoff et al. | |

(Continued)

FOREIGN PATENT DOCUMENTS

| | | |
|---|---|---|
| EP | 1418409 | 4/2006 |
| EP | 2241907 | 10/2010 |

*Primary Examiner* — Isiaka O Akanbi
(74) *Attorney, Agent, or Firm* — Khin K. Chin; Bret E. Field; Bozicevic, Field & Francis LLP

(57) ABSTRACT

Systems for detecting light (e.g., in a flow stream) are described. Light detection systems according to embodiments include two or more photodetector arrays and an optical adjustment component positioned in an optical path between the photodetector arrays. Systems and methods for measuring light emitted by a sample (e.g., in a flow stream) and kits having two or more photodetector arrays and an optical adjustment component are also provided.

20 Claims, 5 Drawing Sheets

(56) References Cited

U.S. PATENT DOCUMENTS

| | | | |
|---|---|---|---|
| 6,249,348 B1 | 6/2001 | Jung et al. | |
| 6,362,888 B1 | 3/2002 | Jung et al. | |
| 6,461,058 B1 | 10/2002 | Birch et al. | |
| 6,490,038 B1 | 12/2002 | Jung et al. | |
| 6,683,314 B2 * | 1/2004 | Oostman, Jr. | G01J 3/02 250/459.1 |
| 6,870,165 B2 | 3/2005 | Amirkhanian et al. | |
| 6,870,976 B2 | 3/2005 | Chen et al. | |
| 7,038,778 B2 | 5/2006 | Yamauchi | |
| 7,129,505 B2 | 10/2006 | Oostman, Jr. et al. | |
| 7,466,419 B2 | 12/2008 | Yamauchi et al. | |
| 7,623,243 B2 * | 11/2009 | Kato | G01J 3/02 356/416 |
| 7,990,525 B2 | 8/2011 | Kanda | |
| 8,149,402 B2 | 4/2012 | Rich et al. | |
| 8,284,402 B2 * | 10/2012 | Frazier | A61B 5/0059 356/419 |
| 8,488,244 B1 * | 7/2013 | Li | G02B 27/1006 359/618 |
| 8,599,487 B2 | 12/2013 | Von Elm et al. | |
| 9,157,791 B2 | 10/2015 | Heimbuch et al. | |
| 10,187,175 B2 * | 1/2019 | Iwasaki | G02B 6/2938 |
| 2002/0071121 A1 * | 6/2002 | Ortyn | C07K 1/047 356/419 |
| 2003/0048539 A1 | 3/2003 | Oostman et al. | |
| 2004/0070765 A1 * | 4/2004 | Yamauchi | G01J 3/26 356/451 |
| 2005/0201501 A1 | 4/2005 | Belotserkovsky et al. | |
| 2006/0102828 A1 | 5/2006 | Furusato et al. | |
| 2009/0121154 A1 | 5/2009 | Westphal et al. | |
| 2009/0201501 A1 | 8/2009 | Westphal et al. | |

\* cited by examiner

LIGHT DETECTION SYSTEMS AND METHODS FOR USING THEREOF

CROSS-REFERENCE TO RELATED APPLICATION

Pursuant to 35 U.S.C. § 119(e), this application claims priority to the filing date of U.S. Provisional Patent Application Ser. No. 62/464,282 filed Feb. 27, 2017; the disclosure of which application is incorporated herein by reference.

INTRODUCTION

Light detection is often used to characterize components of a sample (e.g., biological samples), for example when the sample is used in the diagnosis of a disease or medical condition. When a sample is irradiated, light can be scattered by the sample, transmitted through the sample as well as emitted by the sample (e.g., by fluorescence). Variations in the sample components, such as morphologies, absorptivity and the presence of fluorescent labels may cause variations in the light that is scattered, transmitted or emitted by the sample. These variations can be used for characterizing and identifying the presence of components in the sample. To quantify these variations, the light is collected and directed to the surface of a detector. The amount of light that reaches the detector can impact the overall quality of the optical signal outputted by the detector. The amount of light that reaches the detector can be raised by increasing the surface area of the detector or by increasing collection of the light from the sample.

One technique that utilizes light detection to characterize the components in a sample is flow cytometry. Using data generated from the detected light, distributions of the components can be recorded and where desired material may be sorted. A flow cytometer typically includes a sample reservoir for receiving a fluid sample, such as a blood sample, and a sheath reservoir containing a sheath fluid. The flow cytometer transports the particles (including cells) in the fluid sample as a cell stream to a flow cell, while also directing the sheath fluid to the flow cell. Within the flow cell, a liquid sheath is formed around the cell stream to impart a substantially uniform velocity on the cell stream. The flow cell hydrodynamically focuses the cells within the stream to pass through the center of a light source in a flow cell. Light from the light source can be detected as scatter or by transmission spectroscopy or can be absorbed by one or more components in the sample and re-emitted as luminescence.

SUMMARY

Aspects of the present disclosure include light detection systems having two or more photodetector arrays. Systems according to certain embodiments include a first photodetector array in optical communication with a second photodetector array, each photodetector array having two or more photodetectors (e.g., photomultiplier tubes) and an optical adjustment component positioned in an optical path between the photodetector arrays. In some embodiments, the optical adjustment component is a collimator that collimates light between photodetector arrays. The optical adjustment component may include a beam splitter or a wavelength separator. An optical adjustment component may also be positioned adjacent to one or more photodetectors in the photodetector arrays. In some instances, a dichroic mirror is positioned adjacent to one or more photodetectors in the photodetector arrays. Systems may include additional photodetector arrays, such as a third photodetector array, a fourth photodetector array, a fifth photodetector array, a sixth photodetector array, a seventh photodetector array, an eighth photodetector array, a ninth photodetector array and including a tenth photodetector array. In these systems, an optical adjustment component (e.g., collimator, beam splitter, wavelength separator) may be positioned between each additional photodetector array. Systems may also include an aligner for aligning and a connector for coupling together two photodetector arrays. In embodiments, the subject light detection systems have a proximal end having an orifice for receiving light and a distal end. In some instances, the proximal end of the light detection system is the first photodetector array.

Aspects of the present disclosure also include systems for measuring light from a sample (e.g., in a flow stream). In certain embodiments, systems include a light source and a light detection system that detects one or more wavelengths of light having a first photodetector array in optical communication with a second photodetector array and an optical adjustment component positioned in an optical path between the photodetector arrays. In some embodiments, systems also include an optical collection system for propagating light to the light detection system. The optical collection system may be a free-space light relay system or may include fiber optics such as a fiber optics light relay bundle. In some embodiments, the system is a flow cytometer.

Aspects of the disclosure also include methods for irradiating a sample (e.g., in a flow stream) in an interrogation field with a light source, collecting and detecting light from the sample with the subject light detection systems and measuring the detected light at one or more wavelengths. In some embodiments, light is collected and propagated to the light detection system by a free-space light relay system. In other embodiments, light is collected and propagated to the light detection system by fiber optics, such as a fiber optics light relay bundle.

Kits including one or more components of the subject light detection systems are also provided. Kits according to certain embodiments, include two or more photodetector arrays and an optical adjustment component for positioning in an optical path between each photodetector array. In embodiments, the optical adjustment component includes a collimator, beam splitter, a wavelength separator or a combination thereof. Kits may also include one or more photodetectors, such as photomultiplier tubes (e.g., metal package photomultiplier tubes).

BRIEF DESCRIPTION OF THE FIGURES

The invention may be best understood from the following detailed description when read in conjunction with the accompanying drawings. Included in the drawings are the following figures.

DETAILED DESCRIPTION

Figure 1:
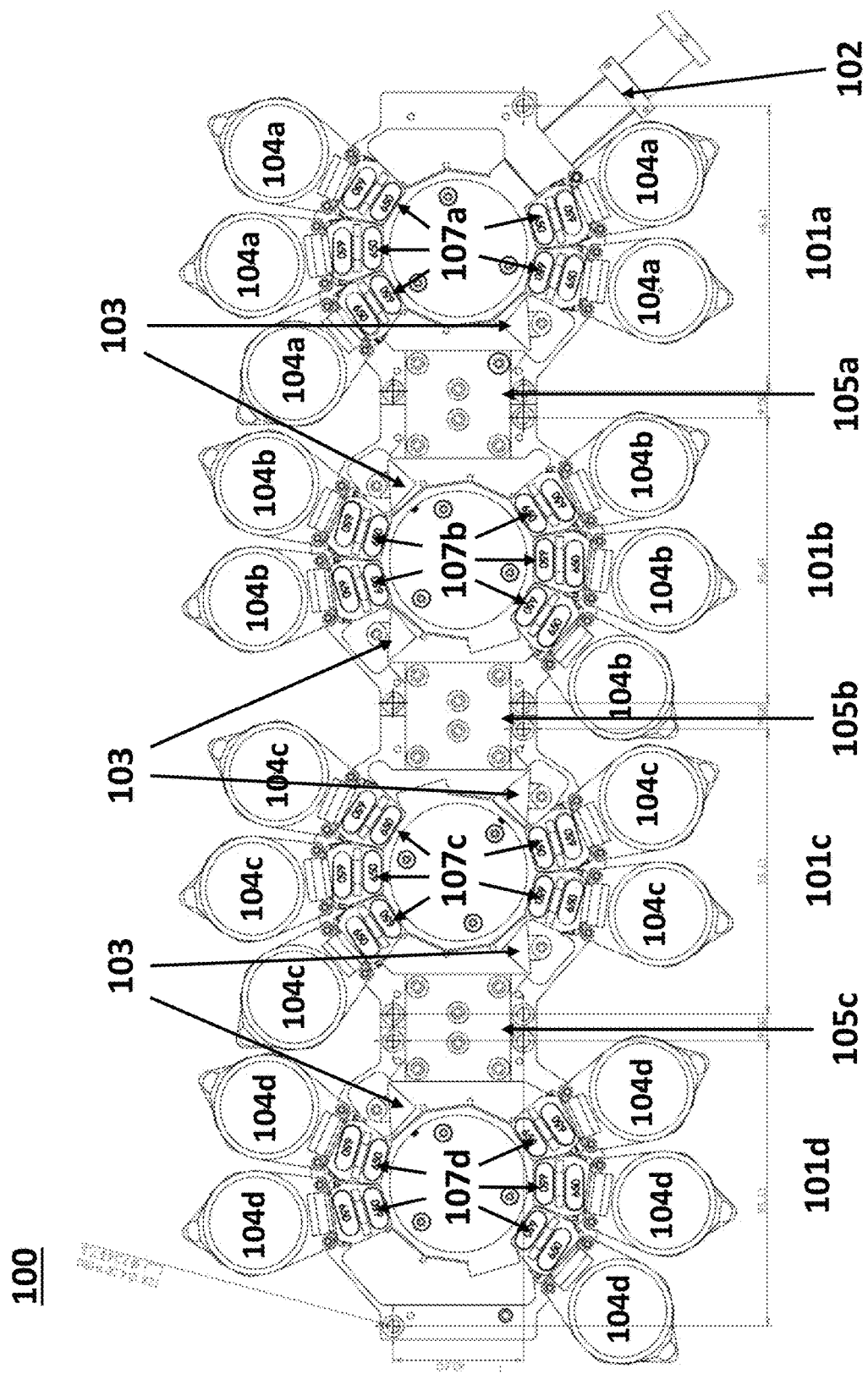
FIG. 1 depicts a light detection system having four photodetector arrays according to certain embodiments.

Systems for detecting light (e.g., in a flow stream) are described. Light detection systems according to embodiments include two or more photodetector arrays and an optical adjustment component positioned in an optical path between the photodetector arrays. Systems and methods for measuring light emitted by a sample (e.g., in a flow stream) and kits having two or more photodetector arrays and an optical adjustment component are also provided.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides light detection systems having two or more photodetector arrays. In further describing embodiments of the disclosure, light detection systems in accordance with embodiments of the invention are described first in greater detail. Next, systems and methods for measuring light emitted by a sample (e.g., in a flow stream) and kits having two or more photodetector arrays and an optical adjustment component are described. Kits having two or more photoedetector arrays and an optical adjustment component for positioned in an optical path between the photodetector arrays are also provided.

Light Detections Systems

Aspects of the present disclosure include light detection systems configured for detecting light emitted by a sample (e.g., in a flow stream of a flow cytometer). As described in greater detail below, light detection systems include two or more photodetector arrays, each photodetector array having photodetectors and an optical adjustment component positioned in an optical path between the photodetector arrays. In some embodiments, systems include a first photodetector array in optical communication with a second photodetector array and an optical adjustment component positioned in an optical path between the first photodetector array and the second photodetector array. In embodiments of the present disclosure, light propagating through the light detection system exhibits little to no divergence. In other words, there is little, if any, change to the light beam as it propagates from one photodetector array to another in the subject light detection systems. In some embodiments, the focal radius of light propagated through the subject light detection systems increases by 5% or less as it propagates from one photodetector array to another, such as 4% or less, such as 3% or less, such as 2% or less, such as 1% or less, such as 0.5% or less, such as 0.1% or less, such as 0.01% or less, such as 0.001% or less and including 0.0001% or less. In certain instances, the focal radius of light propagated through the subject light detection systems does not increase at all (i.e., shows no measureable increase in focal radius) For example, depending on the size of the light beam propagated through the light detection system, the diameter of the beam of light increases by 2 mm or less when it is propagated from one photodetector array to another, such as 1.5 mm or less, such as 1 mm or less, such as 0.9 mm or less, such as 0.8 mm or less, such as 0.7 mm or less, such as 0.6 mm or less, such as 0.5 mm or less, such as 0.4 mm or less, such as 0.3 mm or less, such as 0.2 mm or less, such as 0.1 mm or less, such as 0.05 mm or less, such as 0.01 mm or less, such as 0.001 mm or less, such as 0.0001 mm or less and including 0.00001 mm or less. In certain instances, the diameter of the beam of light exhibits no measurable increase when it is propagated from one photodetector array to another (i.e., increases by 0 mm).

In other embodiments, the intensity of the beam decreases by 25% or less as it propagates from one photodetector array to another, such as 20% or less, such as 15% or less, such as 10% or less, such as 5% or less, such as 1% or less, such as 0.5% or less, such as 0.1% or less, such as 0.01% or less and including 0.001% or less. In certain instances, the intensity of light propagated through the subject light detection systems does not decrease at all (i.e., shows no measureable decrease in intensity) For example, depending on the amount of light propagated through the light detection system, the intensity of the beam of light decreases by 1 mW/cm$^2$ or less when it is propagated from one photodetector array to another, such as 0.5 mW/cm$^2$ or less, such as 0.1 mW/cm$^2$ or less, such as 0.05 mW/cm$^2$ or less, such as 0.01 mW/cm$^2$ or less, such as 0.005 mW/cm$^2$ or less, such as 0.001 mW/cm$^2$ or less, such as 0.0005 mW/cm$^2$ or less, such as 0.0001 mW/cm$^2$ or less, such as 0.00005 mW/cm$^2$ or less and including 0.00001 mW/cm$^2$ or less. In certain instances, there is no measureable decrease in light intensity when it is propagated from one photodetector array to another (i.e., decreases by 0 mW/cm$^2$).

As summarized above, light detection systems include two or photodetector arrays. The term "photodetector array" is used in it conventional sense to refer to an arrangement or series of two or more photodetectors that are configured to detect light. In embodiments, photodetector arrays may include 2 or more photodetectors, such as 3 or more photodetectors, such as 4 or more photodetectors, such as 5 or more photodetectors, such as 6 or more photodetectors, such as 7 or more photodetectors, such as 8 or more photodetectors, such as 9 or more photodetectors, such as 10 or more photodetectors, such as 12 or more photodetectors and including 15 or more photodetectors. In certain embodiments, photodetector arrays include 5 photodetectors. The photodetectors may be arranged in any geometric configuration as desired, where arrangements of interest include, but are not limited to a square configuration, rectangular configuration, trapezoidal configuration, triangular configuration, hexagonal configuration, heptagonal configuration, octagonal configuration, nonagonal configuration, decagonal configuration, dodecagonal configuration, circular configuration, oval configuration as well as irregular shaped configurations. The photodetectors in each photodetector array may be oriented with respect to the other (as referenced in an X-Z plane) at an angle ranging from 10° to 180°, such as from 15° to 170°, such as from 20° to 160°, such as from 25° to 150°, such as from 30° to 120° and including from 45° to 90°.

Light within the each photodetector array may be propagated to the photodetectors in the array by any convenient protocol, such as with mirrors, beam splitters or lenses. Depending on the number of photodetectors in the array, photodetector arrays in some embodiments include dichroic mirrors. In certain embodiments, photodetector arrays of interest include a dichroic mirror adjacent to one or more of the photodetectors in the array, such as a dichroic mirror adjacent to two or more of the photodetectors in the array, such as a dichroic mirror adjacent to three or more of the photodetectors in the array, such as a dichroic mirror adjacent to four or more of the photodetectors in the array, such as a dichroic mirror adjacent to five or more of the photodetectors in the array, such as a dichroic mirror adjacent to six or more of the photodetectors in the array, such as a dichroic mirror adjacent to seven or more of the photodetectors in the array and including a dichroic mirror adjacent to eight or more of the photodetectors in the array. In certain instances, photodetector arrays include a dichroic mirror adjacent to each of the photodetectors in the array. In other embodiments, photodetector arrays include one or more beam splitters for propagating light to each of the photodetectors. For example, the photodetector array may include two or more beam splitters, such as three or more beam splitters, such as four or more beam splitters, such as five or more beam splitters, such as six or more beam splitters, such as seven or more beam splitters, such as eight or more beam splitters, such as nine or more beam splitters and including ten or more beam splitters.

The photodetectors may be any convenient optical sensor, such as active-pixel sensors (APSs), avalanche photodiode, image sensors, charge-coupled devices (CCDs), intensified charge-coupled devices (ICCDs), complementary metal-oxide semiconductor (CMOS) image sensors or N-type metal-oxide semiconductor (NMOS) image sensors, light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other types of photodetectors. In certain embodiments, photodetector arrays include photomultiplier tubes, such as metal package photomultiplier tubes.

Photodetectors of interest are configured to measure collected light at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths.

In some embodiments, photodetectors are configured to measure collected light over a range of wavelengths (e.g., 200 nm-1000 nm). In certain embodiments, detectors of interest are configured to collect spectra of light over a range of wavelengths. For example, systems may include one or more detectors configured to collect spectra of light over one or more of the wavelength ranges of 200 nm-1000 nm. In yet other embodiments, detectors of interest are configured to measure light emitted by a sample in the flow stream at one or more specific wavelengths. For example, systems may include one or more detectors configured to measure light at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, one or more detectors may be configured to be paired with specific fluorophores, such as those used with the sample in a fluorescence assay.

In embodiments, the light detection system is configured to measure light continuously or in discrete intervals. In some instances, detectors of interest are configured to take measurements of the collected light continuously. In other instances, the light detection system is configured to take measurements in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

Light detection systems according to embodiments of the present disclosure include two or more photodetector arrays in optical communication. By "in optical communication" is meant that the photodetector arrays are configured such that light travels between photodetector arrays along one or more optical paths. For example, light may travel between photodetector arrays along two or more optical paths, such as three or more optical paths, such as four or more optical paths and including five or more optical paths. In certain embodiments, light travels along a single optical path across all of the photodetector arrays in the light detection system. As described in greater detail below, the photodetector arrays may be arranged in a linear configuration (i.e., along a single axis) and light is propagated to each photodetector array along a single optical path. In these embodiments, light is propagated through the series of photodetector arrays and terminates at the last photodetector array (e.g., with a beam stop).

In embodiments of the present disclosure, an optical path between each photodetector array includes an optical adjustment component. By "optical adjustment" is meant that light is changed or adjusted when propagated from one photodetector array to another. For example, the optical adjustment may be to change the profile of the light beam, the focus of the light beam, the direction of beam propagation or to collimate the light beam.

In some instances, optical adjustment includes collimating the light. The term "collimate" is used in its conventional sense to refer to the optically adjusting the collinearity of light propagation or reducing divergence by the light of from a common axis of propagation. In some instances, collimating includes narrowing the spatial cross section of a light beam. In other instances, optical adjustment includes changing the direction of the light beam, such as changing the propagation of the light beam by 1° or more, such as by 5° or more, such as by 10° or more, such as by 15° or more, such as by 20° or more, such as by 25° or more, such as by 30° or more, such as by 45° or more, such as by 60° or more, such as by 75° or more and including changing the direction of light propagation by 90° or more. In yet other instances, optical adjustment is a de-magnification protocol so as to decrease the dimensions of the light (e.g., beam spot), such as decreasing the dimensions by 5% or more, such as by 10% or more, such as by 25% or more, such as by 50% or more and including decreasing the dimensions by 75% or more.

Optical adjustment components may be any convenient device or structure which provides the desired change to the light beam and may include, but is not limited to, lenses, mirrors, beam splitters, collimating lenses, pinholes, slits, gratings, light refractors, and any combinations thereof. The light detection system may include one or more optical adjustment components as needed, such as two or more, such as three or more, such as four or more and including five or more optical adjustment components.

In certain embodiments, light detection systems include a collimator in an optical path between each photodetector array. The collimator may be any convenient collimating protocol, such as one or more mirrors or curved lenses or a combination thereof. For example, the collimator is in certain instances a single collimating lens. In other instances, the collimator is a collimating mirror. In yet other instances, the collimator includes two lenses. In still other instances, the collimator includes a mirror and a lens. Where the collimator includes one or more lenses, the focal length of the collimating lens may vary, ranging from 5 mm to 500 mm, such as from 6 mm to 475 mm, such as from 7 mm to 450 mm, such as from 8 mm to 425 mm, such as from 9 mm to 400 mm, such as from 10 mm to 375 mm, such as from 12.5 mm to 350 mm and including a focal length ranging from 15 mm to 300 mm. In certain embodiments, the focal length ranges from 400 mm to 500 mm, such as from 405 mm to 475 mm, such as from 410 mm to 450 mm and including from 410 mm to 425 mm, such as 410 mm or 420 mm.

In certain embodiments, the optical adjustment component includes a wavelength separator. The term "wavelength separator" is used herein in its conventional sense to refer to an optical protocol for separating polychromatic light into its component wavelengths. Wavelength separation, according to certain embodiments, may include selectively passing or blocking specific wavelengths or wavelength ranges of the polychromatic light. Wavelength separation protocols of interest which may be a part of or combined with the subject flow cell nozzles, include but are not limited to, colored glass, bandpass filters, interference filters, dichroic mirrors, diffraction gratings, monochromators and combinations thereof, among other wavelength separating protocols. In some embodiments, the wavelength separator is an optical filter. For example, the optical filter may be a bandpass filter having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm.

In the subject light detection systems, the optical adjustment component may be separate from the photodetector array, such as at a position between photodetector arrays or may be physically coupled to one or more of the photodetector arrays. In one example, the optical adjustment component is coupled to one or more of the photodetector arrays with a permanent or non-permanent adhesive or affixed with a fastener, such as a hook and loop fasteners, magnets, latches, screws, notches, countersinks, counter-bores, grooves, pins, tethers, hinges, Velcro or any combination thereof. In certain instances, the optical adjustment component is releasably attached. The term "releasably" is used herein in its conventional sense to mean that the optical adjustment component may be freely detached and re-attached from the light detection system. In other instances, the optical adjustment component is co-molded to one or more of the photodetector arrays. In yet another example, the optical adjustment component is integrated directly into one or more of the photodetector arrays.

In certain embodiments, photodetector arrays in the subject systems include a housing with two or more photodetectors positioned within the housing where the housing includes a wall having an orifice for light to propagate to the photodetectors of the photodetector array. Depending on the size of the photodetector array, the orifice may range from 0.01 cm$^2$ to 10 cm$^2$, such as from 0.05 cm$^2$ to 9 cm$^2$, such as from, such as from 0.1 cm$^2$ to 8 cm$^2$, such as from 0.5 cm$^2$ to 7 cm$^2$ and including from 1 cm$^2$ to 5 cm$^2$. In certain embodiments, the housing has one or more additional orifices for light to propagate out of the photodetector to another photodetector array in the subject light detection system. For example, the housing may include a second wall having an orifice for light to propagate to another photodetector array. As described in greater detail below, one or more walls of the photodetector array housing, in certain embodiments, may be detached in order to connect an additional photodetector array to the light detection system.

Photodetector arrays may be releasably connected together in the subject light detection systems. The term "releasably" is used herein in its conventional sense such that each photodetector array may be freely detached and re-attached. Photodetector arrays may be connected by any convenient protocol. In certain embodiments, photodetector arrays are connected together with a fastener, such as a hook and loop fasteners, magnets, latches, notches, countersinks, counter-bores, grooves, pins, tethers, hinges, Velcro, non-permanent adhesives or a combination thereof. In certain instances, a first photodetector array is connected to a second photodetector array by screw threading the two photodetector arrays together. In other instances, a first photodetector array is connected to a second photodetector array by slot-fitting a protrusion into a groove. In yet other instances, a first photodetector array is connected to a second photodetector array by one or more screws.

In some embodiments, to couple a first photodetector array to a second photodetector array, aligners on the outer walls of the first photodetector array housing are placed into contact with aligners on the second photodetector array housing. The housing of the photodetector array may include 2 or more aligners, such as 3 or more aligners, such as 4 or more aligners, such as 5 or more aligners, such as 7 or more aligners and including 10 or more aligners. Any suitable type of aligner may be employed, such as an alignment protrusion, an alignment rail, an alignment notch, an alignment groove, an alignment slot, an alignment countersink, an alignment counter-bore, an alignment recess, an alignment hole or a combination thereof. The shape of aligners may vary, where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In some embodiments, the aligners are cylindrically shaped. In other embodiments, the aligners are spherical. In yet other embodiments, the aligners are polygonal-shaped, such as square-shaped or rectangular. The width of each aligner may vary, ranging in some instances from 1 mm to 25 mm, such as from 2 mm to 22 mm, such as from 3 mm to 20 mm, such as from 4 mm to 17 mm and including from 5 mm to 15 mm. The length of each aligner positioned at the distal end of the mount ranges from 1 mm to 50 mm, such as from 2 mm to 45 mm, such as from 3 mm to 40 mm, such as from 4 m to 35 mm, such as from 5 mm to 30 mm and including from 10 mm to 20 mm. Where the aligner positioned is an alignment recess, such as a notch, a countersink, a counter-bore, a slot, a groove or a hole, the depth of the aligner may range from 1 mm to 50 mm, such as from 2 mm to 45 mm, such as from 3 mm to 40 mm, such as from 4 m to 35 mm, such as from 5 mm to 30 mm and including from 10 mm to 20 mm.

Where the photodetector array housing includes more than one aligner, the distance between each aligner may vary, being spaced apart by 2 mm or more, such as by 3 mm or more, such as by 5 mm or more, such as by 7 mm or more, such as by 10 mm or more and including by 25 mm or more. Where the photodetector array housing includes three or more aligners, the distance between each aligner may be the same or different or a combination thereof. In some embodiments, the distance between each aligner is different. In other embodiments, each aligner is spaced equidistant from each other. In certain embodiments, the photodetector array housing includes 4 aligners that are positioned equidistantly spaced along the outer edge of a wall of the photodetetor housing.

In some embodiments, when the aligners of a first photodetector array are coupled to the aligners of a second photodetector array, the optical components of the photodetector arrays are optically aligned and form a complete optical path between photodetector arrays. In other words, in these embodiments when the aligners of the first photodetector array are not coupled to the aligners of the second photodetector array, a complete optical path between the first photodetector array and the second photodetector array is not complete and light does not completely propagate from the first photodetector array to the photodetectors of the second photodetector array. For example, when the aligners of the first photodetector array are not sufficiently coupled to the aligners of the second photodetector array, light from the first photodetector array may propagate only to 90% or less of the photodetectors of the second photodetector array, such as 80% or less, such as 70% or less, such as 60% or less, such as 50% or less, such as 40% or less, such as 30% or less, such as 25% or less, such as 20% or less and including to 10% or less of the photodetectors of the second photodetector array. Depending on the number of photodetectors in the subject photodetector arrays, light may be propagate to 10 or less of the photodetectors in the second photodetector array, such as 9 or less, such as 8 or less, such as 7 or less, such as 6 or less, such as 5 or less, such as 4 or less, such as 3 or less, such as 2 or less and including 1 or less of the photodetectors. In certain embodiments, when the aligners of the first photodetector array are not sufficiently coupled to the aligners of the second photodetector array, light from the first photodetector array does not reach any of the photodetectors in the second photodetector array.

In some embodiments, when a first photodetector array is coupled to a second photodetector array, a mirror in the first photodetector array is optically aligned with a mirror in the second photodetector array such that light from the first photodetector array is propagated into the second photodetector array. In another example, when a first photodetector array is coupled to a second photodetector array, a beam splitter in the first photodetector array is optically aligned with a mirror in the second photodetector array. In still another example, when a first photodetector array is coupled to a second photodetector array, a mirror in the photodetector array is optically aligned with a collimating lens in the second photodetector array.

As summarized above, light detection systems include two or photodetector arrays. Depending on the type of light being detected, the number of photodetector arrays may vary as desired, and may be three or more photodetector arrays, such as four or more, such as five or more, such as six or more, such as seven or more, such as eight or more, such as nine or more, such as ten or more, such as eleven or more, such as twelve or more, such as thirteen or more, such as fourteen or more and including fifteen or more photodetector arrays. As summarized above, the photodetector arrays in the subject light detection systems are in optical communication. As such, light from each photodetector array is propagated to other photodetector arrays in the subject light detection systems.

The photodetector arrays may be arranged in any geometric configuration as desired, where arrangements of interest include, but are not limited to a linear configuration, star-shaped configuration, a triangular configuration, a square configuration, rectangular configuration, trapezoidal configuration, triangular configuration, hexagonal configuration, heptagonal configuration, octagonal configuration, nonagonal configuration, decagonal configuration, dodecagonal configuration, circular configuration, oval configuration as well as irregular shaped configurations.

The photodetector arrays may be arranged along one or more axis. In embodiments, the photodetector arrays may be oriented with respect to the other (as referenced in an X-Z plane) at an angle ranging from 0° to 180°, such as from 10° to 170°, such as from 20° to 160°, such as from 25° to 150°, such as from 30° to 120° and including from 45° to 90°. In embodiments, the photodetector arrays may be arranged with respect to each other at an angle that is the same or different depending on the number of photodetector arrays and the optical adjustment component positioned between the photodetector arrays. For example, in certain instances the angle between a first photodetector array and a second photodetector array is the same as the angle between the second photodetector array and a third photodetector array. In some embodiments, the angle between a first photodetector array and a second photodetector array are different than the angle between the second photodetector array and a third photodetector array.

Figure 4:
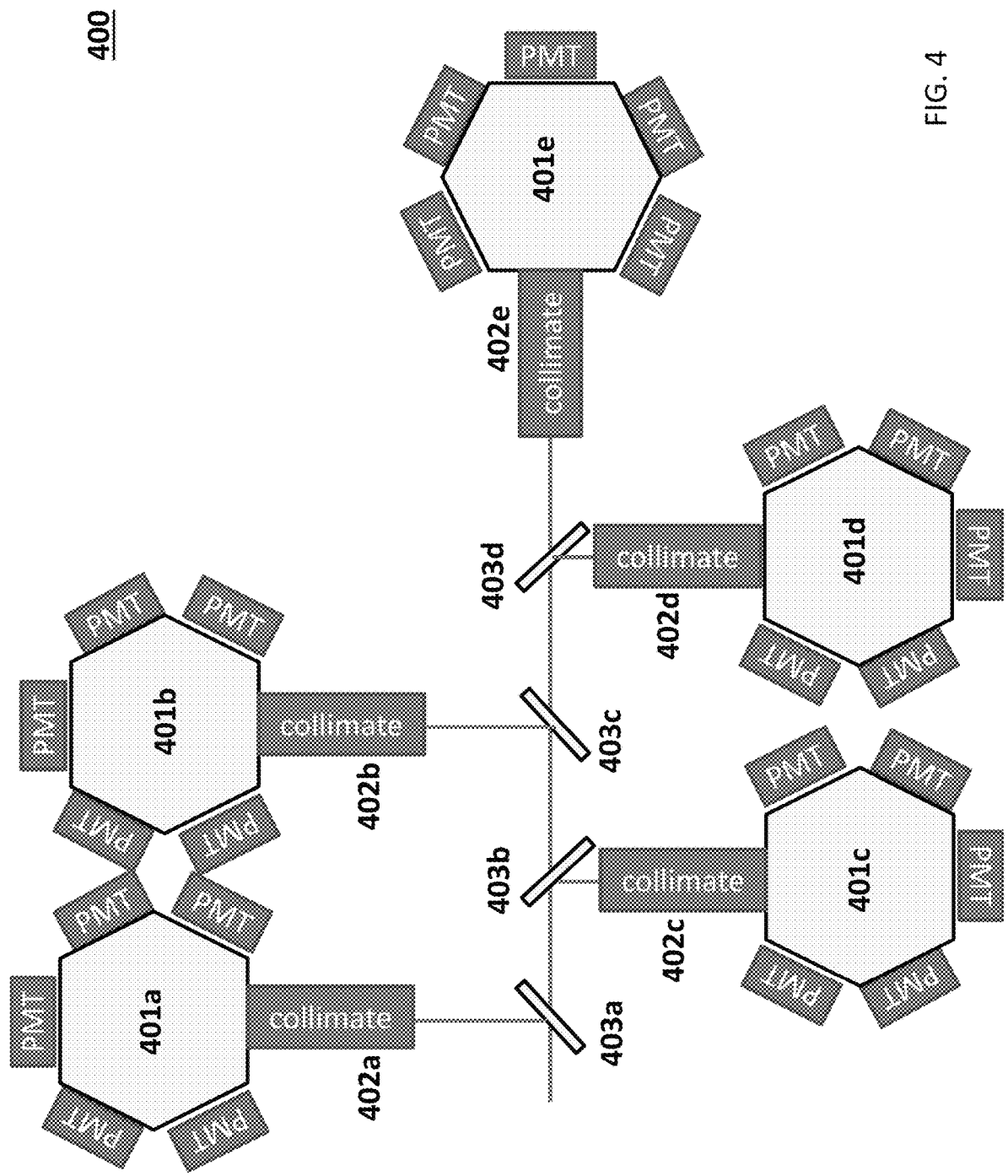
FIG. 4 depicts a light detection system having an arrangement of photodetector arrays according to another embodiment of the present disclosure.

FIG. 4 depicts a light detection system having an arrangement of photodetector arrays according to another embodiment of the present disclosure. Light detection system 400 includes five photodetector arrays 401a, 401b, 401c, 401d and 401e. Photodetector array 401a is an optical detector with the incident light collection component (e.g., fiber optical light collector, free-space relay collector, not shown) through dichroic mirror 403a which passes light to photodetector array 401a through collimator 402a. Light passing through dichroic mirror 403a is propagated to a second dichroic mirror 403b which passes light to dichroic mirror 403c and to collimator 402c into photodetector array 401c. Light from dichroic mirror 403c is propagated to collimator 402b and into photodetector array 401b while light passing through dichroic mirror 403c is propagated to dichroic mirror 403d which further propagates the light through collimator 402d and into photodetector array 401d. Light passing through dichroic mirror 403d is propagated to collimator 402e and into photodetector array 401e, which may further include a beam stop (not shown).

In some embodiments, the photodetector arrays are arranged along two or more parallel axes, such as along three or more, such as four or more, such as five or more, such as six or more, such as seven or more, such as eight or more, such as nine or more and including ten or more parallel axes. In some instances, each parallel axis may include the same number of photodetector arrays. In other instances, each parallel axis may include a different number or photodetector arrays. Each axis may include one or more photodetector array, such as two or more photodetector arrays, such as three or more photodetector arrays, such as four or more photodetector arrays and including five or more photodetector arrays. The photodetector arrays positioned along the different axes are in optical communication through an optical adjustment component, as described above, such as a beam splitter or a dichroic mirror.

In certain embodiments, light detection systems include photodetector arrays that are concentrically arranged. The term concentric is used herein in its conventional sense to refer to an arrangement where each photodetector arrays is positioned equidistantly from a central point in the subject light collection system. In some instances, the center of each photodetector array is equidistant from a central point of the light detection system. In other instances, the entry orifice into each photodetector array is equidistant from a central point of the light detection system. The central point may include one or more optical adjustment components as described above (e.g., beam splitter, dichroic mirrors, collimating lenses, etc.)

In these embodiments, three or more photodetector arrays may be concentrically arranged, such as four or more photodetector arrays and including five or more concentrically arranged photodetector arrays. In certain instances, all of the photodetector arrays in the light detection system may be concentrically arranged. In other instances, light detection systems may include one or more groups of photodetector arrays which are concentrically arranged and one or more groups of photodetector arrays which are arranged in some other geometric configuration as described above. For example, in some embodiments, light detection systems of interest include a first group of photodetector arrays that are concentrically arranged and a second group of photodetector arrays that are arranged in a different configuration, such as being linearly arranged.

Figure 5:
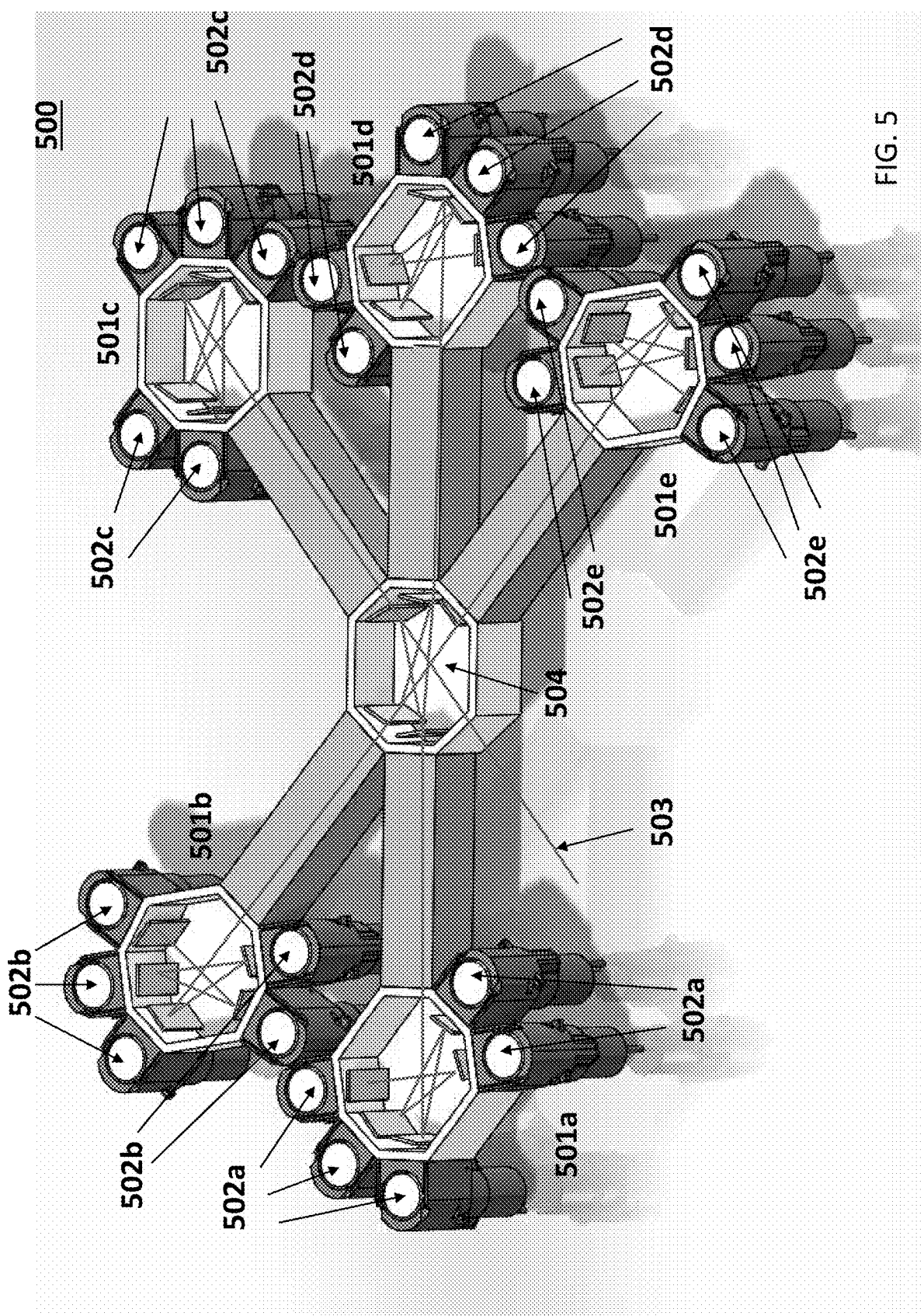
FIG. 5 depicts a light detection system having an arrangement of photodetector arrays according to another embodiment of the present disclosure.

FIG. 5 depicts a light detection system having an arrangement of photodetector arrays according to another embodiment of the present disclosure. Light detection system 500 includes five photodetector arrays, 501a, 501b, 501c, 501d and 501e that are concentrically arranged around central compartment 504 having optical adjustment components that relay light to each of photodetector arrays 501a, 501b, 501c, 501d and 501e. Each photodetector array includes light detectors 502a, 502b, 502c, 502d and 502e with a dichroic mirror positioned adjacent to each photodetector. Light is propagated to light detection system as shown along light beam path 503. Depending on the configuration of the photodetector arrays, the intensity of the propagated beam decreases by 25% or less as it propagates from one photodetector array to another, such as 20% or less, such as 15% or less, such as 10% or less, such as 5% or less, such as 1% or less, such as 0.5% or less, such as 0.1% or less, such as 0.01% or less and including 0.001% or less. In certain instances, the intensity of light propagated through the subject light detection systems does not decrease at all (i.e., shows no measureable decrease in intensity). In certain embodiments, the photodetector arrays are arranged such that the intensity of light detected by the photodetectors of each photodetector array will vary, by 10% or less, such as 5% or less, such as 4% or less, such as 3% or less, such as 2% or less, such as 1 or less, such as 0.5% or less, such as 0.1% or less, such as 0.01% or less and including 0.001% or less.

In certain embodiments, the photodetector arrays are arranged linearly along a single axis. In these embodiments, light is serially propagated through each photodetector array. For instance, in one example the subject light detection system includes two photodetector arrays and light is propagated from the first photodetector array to the second photodetector array. In another example, the light detection system includes three photodetector arrays and light is propagated from the first photodetector array to the second photodetector array and then to the third photodetector array. In still another example, the light detection system includes four photodetector arrays and light is propagated from the first photodetector array to the second photodetector array to the third photodetector array and then to the fourth photodetector array. In certain embodiments, light detection systems of interest include 10 or more photodetector arrays that are linearly arranged and light propagates serially from the first photodetector array to the last photodetector array in the linear arrangement.

In some embodiments, light detection systems propagate light to each of the photodetector arrays with one or more dichroic mirrors along the optical path between the photodetector arrays. For example, light detection systems may include 2 or more dichroic mirrors, such as 3 or more dichroic mirrors, such as 4 or more dichroic mirrors, such as 5 or more dichroic mirrors, such as 6 or more dichroic mirrors, such as 7 or more dichroic mirrors, such as 8 or more dichroic mirrors, such as 9 or more dichroic mirrors and including 10 or more dichroic mirrors. In certain instances, the photodetector arrays are arranged such that the ratio of the number of detectors to the number of dichroic mirrors positioned along the optical path between photodetector arrays is 3:1 or more, such as 3.5:1 or more, such as 4:1 or more, such as 4.5:1 or more, such as 5:1 or more, such as 5.5:1 or more, such as 6:1 or more, such as 6.5:1 or more and including a ratio of 7:1 or more. In one example, light detection systems include 16 detectors and 4 dichroic mirrors along the optical path. In another example, light detection systems include 32 detectors and 5 dichroic mirrors along the optical path. In yet another example, light detection systems include 25 detectors and 8 dichroic mirrors along the optical path.

In some embodiments light received by the first photodetector array may be conveyed to the first photodetector array by an optical collection system. The optical collection system may be any suitable light collection protocol that collects and directs the light to the first photodetector array. In some embodiments, the optical collection system includes fiber optics, such as a fiber optics light relay bundle. In other embodiments, the optical collection system is a free-space light relay system.

In embodiments, the optical collection system may be physically coupled to the first photodetector array, such as with an adhesive, co-molded together or integrated into the first photodetector array. In certain embodiments, the optical collection system and first photodetector array are integrated into a single unit. In some instances, the optical collection system is coupled to the first photodetector array with an connector that fastens the optical collection system to the first photodetector array, such as with a hook and loop fasteners, magnets, latches, notches, countersinks, counterbores, grooves, pins, tethers, hinges, Velcro, non-permanent adhesives or a combination thereof.

In other embodiments, the first photodetector array and the optical collection system are in optical communication, but are not physically in contact. In embodiments, the optical collection system may be positioned 0.001 mm or more from the first photodetector array, such as 0.005 mm or more, such as 0.01 mm or more, such as 0.05 mm or more, such as 0.1 mm or more, such as 0.5 mm or more, such as 1 mm or more, such as 10 mm or more, such as 25 mm or more, such as 50 mm or more and including 100 mm or more from the first photodetector array.

In certain embodiments, the optical collection system includes fiber optics. For example, the optical collection system may be a fiber optics light relay bundle and light is conveyed through the fiber optics light relay bundle to the first photodetector array. Any fiber optics light relay system may be employed to propagate light to the first photodetector array. In certain embodiments, suitable fiber optics light relay systems for propagating light to the first photodetector array include, but are not limited to, fiber optics light relay systems such as those described in U.S. Pat. No. 6,809,804, the disclosure of which is herein incorporated by reference.

In other embodiments, the optical collection system is a free-space light relay system. The phrase "free-space light relay" is used herein in its conventional sense to refer to light propagation that employs a configuration of one or more optical components to direct light to the first photodetector array through free-space. In certain embodiments, the free-space light relay system includes a housing having a proximal end and a distal end, the proximal end being coupled to the first photodetector array. The free-space relay system may include any combination of different optical adjustment components, such as one or more of lenses, mirrors, slits, pinholes, wavelength separators, or a combination thereof. For example, in some embodiments, free-space light relay systems of interest include one or more focusing lens. In other embodiments, the subject free-space light relay systems include one or more mirrors. In yet other embodiments, the free-space light relay system includes a collimating lens. In certain embodiments, suitable free-space light relay systems for propagating light to the first photodetector array, but are not limited to, light relay systems such as those described in U.S. Pat. Nos. 7,643,142; 7,728,974 and 8,223,445, the disclosures of which is herein incorporated by reference.

FIG. 1 depicts a light detection system 100 according to certain embodiments. Light is propagated to the first photodetector array 101a of light detection system 100 through optical collection system 102. Photodetector array 101a includes five photodetectors 104a, each having an optical adjustment component 107a for adjusting one or more properties of light propagated through photodetector array 101a. Light from photodetector array 101a is propagated to a second photodetector array 101b through optical adjustment component 103. Photodetector array 101b includes photodetectors 104b and light adjustment components 107b. Photodetector array 101a is aligned and physically coupled to photodetector array 101b with fastener 105a. Light from photodetector array 101b is further propagated to a third photodetector array 101c through optical adjustment component 103. Photodetector array 101c includes photodetectors 104c and light adjustment components 107c. Photodetector array 101b is also aligned and physically coupled to photodetector array 101c with fastener 105b. Light detection system 100 according to this embodiment includes a fourth photodetector array 101d. Light from photodetector array 101c is propagated to photodetector array 101d through optical adjustment component 103 to photodetectors 104d through light adjustment components 104d. Fastener 105c aligns and connects photodetector array 101d to photodetector array 101c.

Figure 2:
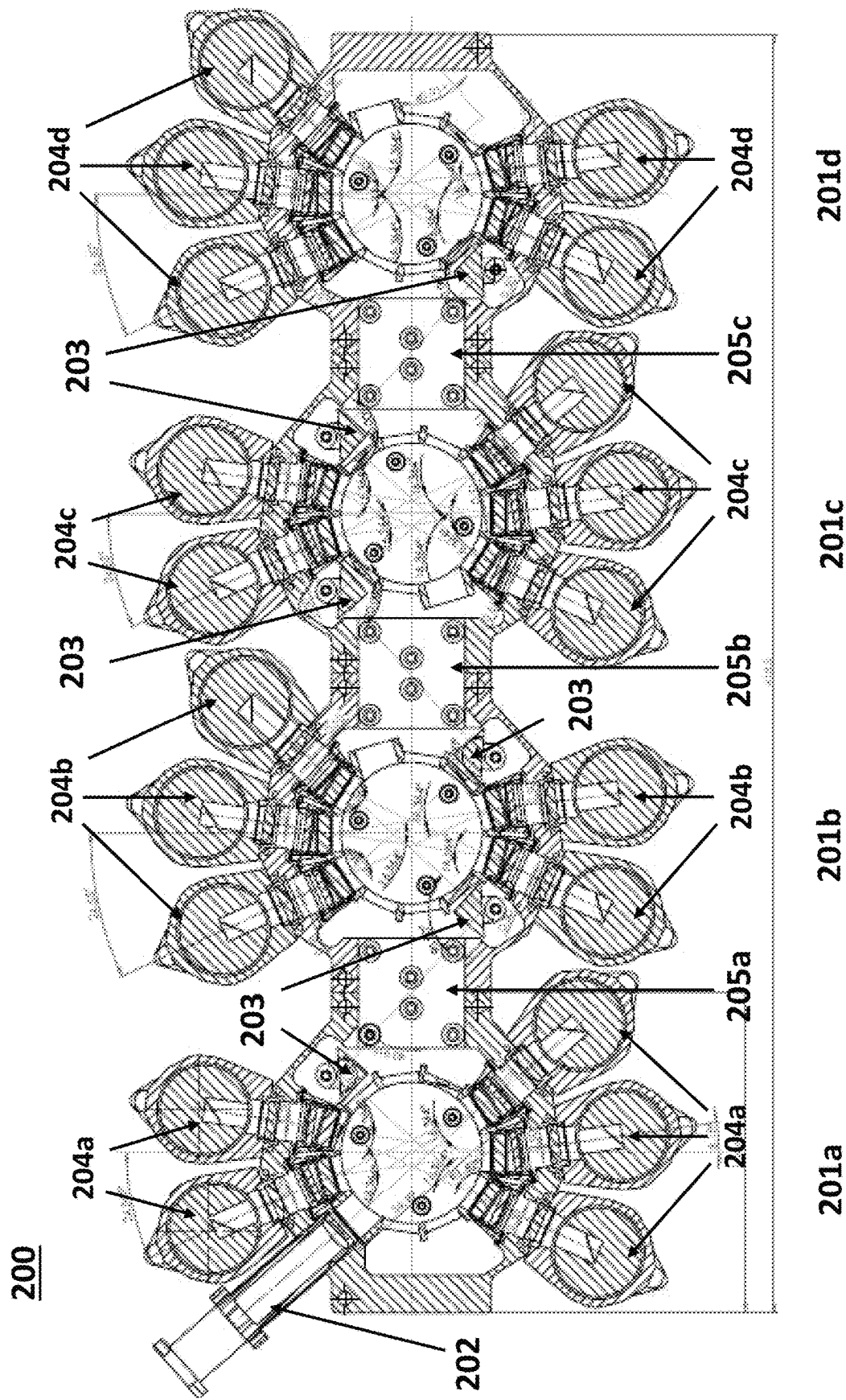
FIG. 2 depicts a light detection system along with an example optical path through the light detection system according to certain embodiments of the present disclosure.

FIG. 2 depicts a light detection system 200 according to certain embodiments showing an example optical path through the light detection system. First photodetector array 201a receives light through optical collection system 202. Photodetector array 201a detects light with photodetectors 204a. Light from photodetector array 201a is propagated to a second photodetector array 201b through optical adjustment component 203. Photodetector array 201b includes photodetectors 204b to detect propagated light. Photodetector array 201a is aligned and physically coupled to photodetector array 201b with fastener 205a. Light from photodetector array 201b is further propagated to photodetector array 201c having photodetectors 204c through optical adjustment component 203. Photodetector array 201b is also aligned and physically coupled to photodetector array 201c with fastener 205b. Light detection system 200 includes a fourth photodetector array 201d. Light from photodetector array 201c is propagated to photodetector array 201d through optical adjustment component 203 to photodetectors 204d through light adjustment components 204d. Fastener 205c aligns and connects photodetector array 201d to photodetector array 201c.

Figure 3:
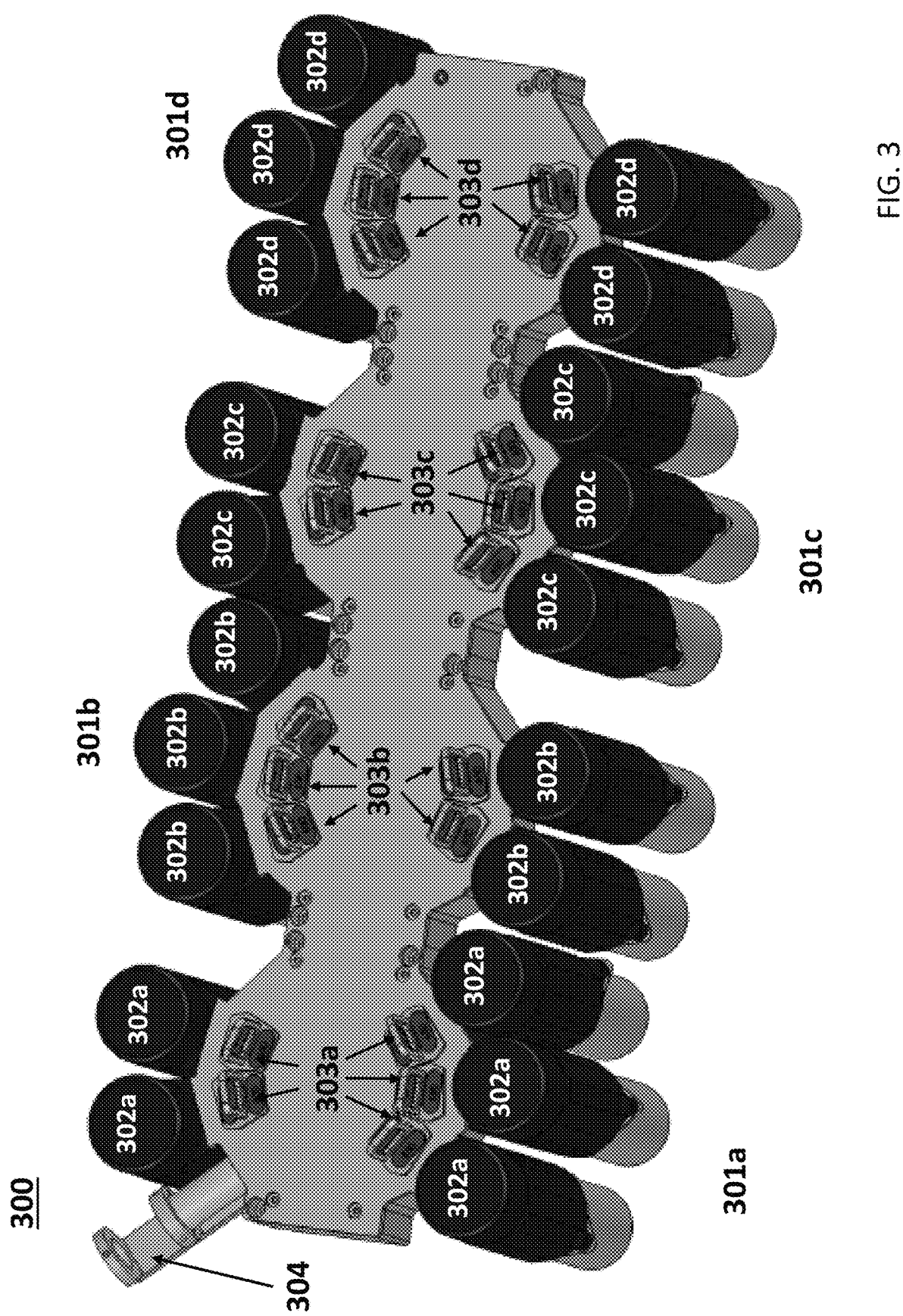
FIG. 3 is a three dimensional depiction of a light detection system according to certain embodiments of the present disclosure.

FIG. 3 is a three dimensional depiction of a light detection system according to certain embodiments. Light detection system 300 is enclosed in a housing having four linearly positioned photodetector arrays 301a, 301b, 301c and 301d. Photodetector array 301a detects received light from light collection pathway 304 and detects light with photodetectors 302a. Light is propagated through photodetector array 301b and detected with photodetectors 302b, through photodetector array 301c and detected with photodetectors 302c and to photodetector array 301d and detected with photodetectors 302d. Light detected by photodetectors 302a, 302b, 302c and 302d are adjusted with light adjustment components 303a, 303b, 303c and 303d, respectively. An optical adjustment component (e.g., collimator) is positioned inside of the house (not shown): between photodetector arrays 301a and 301b; between photodetector arrays 301b and 301c and between photodetector arrays 301c and 301d.

Systems for Measuring Light Emitted by a Sample

Aspects of the present disclosure also include systems for measuring light from a sample (e.g., in the flow stream in a flow cytometer). In certain embodiments, systems include a light source and a light detection system having two or more photodetector arrays, as described above. For example, systems of interest may include a light source and a first photodetector array in optical communication with a second photodetector array, each photodetector array having two or more photodetectors (e.g., photomultiplier tubes) and an optical adjustment component positioned in an optical path between the photodetector arrays. In some embodiments, the system is a flow cytometer. In some instances, the light detection system having the photodetector arrays is non-releasably integrated into the flow cytometer. In certain embodiments, the light detection system is in optical communication with the source of sample (e.g., the flow stream in a flow cytometer) through an optical collection system (e.g., fiber optics or free-space light relay system).

Systems of interest for measuring light from a sample include a light source. In embodiments, the light source may be any suitable broadband or narrow band source of light. Depending on the components in the sample (e.g., cells, beads, non-cellular particles, etc.), the light source may be configured to emit wavelengths of light that vary, ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a narrow band light source emitting a wavelength ranging from 200 nm to 900 nm. For example, the light source may be a narrow band LED (1 nm-25 nm) emitting light having a wavelength ranging between 200 nm to 900 nm. In some embodiments, the light source is a laser, such as continuous wave laser. For example, the laser may be a helium-neon (HeNe) laser. In certain embodiments, the light source is a laser in a flow cytometer.

In other embodiments, the light source is a non-laser light source, such as a lamp, including but not limited to a halogen lamp, deuterium arc lamp, xenon arc lamp, a light-emitting diode, such as a broadband LED with continuous spectrum, superluminescent emitting diode, semiconductor light emitting diode, wide spectrum LED white light source, an multi-LED integrated. In some instances the non-laser light source is a stabilized fiber-coupled broadband light source, white light source, among other light sources or any combination thereof.

The light source may be positioned any suitable distance from the sample (e.g., the flow stream in a flow cytometer), such as at a distance of 0.001 mm or more from the flow stream, such as 0.005 mm or more, such as 0.01 mm or more, such as 0.05 mm or more, such as 0.1 mm or more, such as 0.5 mm or more, such as 1 mm or more, such as 5 mm or more, such as 10 mm or more, such as 25 mm or more and including at a distance of 100 mm or. In addition, the light source irradiate the sample at any suitable angle (e.g., relative the vertical axis of the flow stream), such as at an angle ranging from 10° to 90°, such as from 15° to 85°, such as from 20° to 80°, such as from 25° to 75° and including from 30° to 60°, for example at a 90° angle.

The light source may be configured to irradiate the sample continuously or in discrete intervals. In some instances, systems include a light source that is configured to irradiate the sample continuously, such as with a continuous wave laser that continuously irradiates the flow stream at the interrogation point in a flow cytometer. In other instances, systems of interest include a light source that is configured to irradiate the sample at discrete intervals, such as every 0.001 milliseconds, every 0.01 milliseconds, every 0.1 milliseconds, every 1 millisecond, every 10 milliseconds, every 100 milliseconds and including every 1000 milliseconds, or some other interval. Where the light source is configured to irradiate the sample at discrete intervals, systems may include one or more additional components to provide for intermittent irradiation of the sample with the light source. For example, the subject systems in these embodiments may include one or more laser beam choppers, manually or computer controlled beam stops for blocking and exposing the sample to the light source.

In embodiments, light emitted by the sample is propagated to the subject light detection systems (as described above), having two or more photodetector arrays. As described above, photodetectors in the subject photodetector arrays may include, but are not limited to optical sensors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. For example, the light collection system for measuring light from a sample may include photodetectors arrays having 2 photodetectors or more, such as 3 photodetectors or more, such as 4 photodetectors or more, such as 5 photodetectors or more, such as 10 photodetectors or more, such as 25 photodetectors or more and including 50 photodetectors or more. In certain embodiments, systems include photodetector arrays with 5 photodetectors.

In embodiments of the present disclosure, detectors of interest are configured to measure collected light at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths.

In some embodiments, detectors of interest are configured to measure collected light over a range of wavelengths (e.g., 200 nm-1000 nm). In certain embodiments, detectors of interest are configured to collect spectra of light over a range of wavelengths. For example, systems may include one or more detectors configured to collect spectra of light over one or more of the wavelength ranges of 200 nm-1000 nm. In yet other embodiments, detectors of interest are configured to measure light emitted by a sample in the flow stream at one or more specific wavelengths. For example, systems may include one or more detectors configured to measure light at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, one or more detectors may be configured to be paired with specific fluorophores, such as those used with the sample in a fluorescence assay.

In embodiments, the detector is configured to measure light continuously or in discrete intervals. In some instances, detectors of interest are configured to take measurements of the collected light continuously. In other instances, detectors of interest are configured to take measurements in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

In some embodiments, systems for measuring light from sample include a light collection system for collecting and directing light from the sample source (e.g., flow stream) to the photodetector arrays of the subject light detections systems. The optical collection system may be physically coupled to the first photodetector array, such as with an adhesive, co-molded together or integrated into the first photodetector array. In certain embodiments, the optical collection system and the light detection system are integrated into a single unit. In other embodiments, the optical collection system is coupled to the first photodetector array of the light detection system with an connector, such as with a hook and loop fasteners, magnets, latches, notches, countersinks, counter-bores, grooves, pins, tethers, hinges, Velcro, non-permanent adhesives or a combination thereof.

In other embodiments, the light detection system and the optical collection system are in optical communication, but are not physically in contact. For example, the optical collection system may be positioned 0.001 mm or more from the first photodetector array, such as 0.005 mm or more, such as 0.01 mm or more, such as 0.05 mm or more, such as 0.1 mm or more, such as 0.5 mm or more, such as 1 mm or more, such as 10 mm or more, such as 25 mm or more, such as 50 mm or more and including 100 mm or more from the light detection system.

In some embodiments, the optical collection system includes fiber optics. For example, in some instances the optical collection system may be a fiber optics light relay bundle and light is conveyed through the fiber optics light relay bundle to the first photodetector array. In other embodiments, the optical collection system is a free-space light relay system. For instance, the free-space light relay system may include a housing having a proximal end and a distal end, the proximal end being coupled to the first photodetector array. The free-space relay system may include any combination of different optical adjustment components, such as one or more lenses, mirrors, slits, pinholes, wavelength separators, or a combination thereof.

In certain embodiments, the subject systems are flow cytometric systems employing the above described light detection system for detecting light emitted by a sample in a flow stream. Suitable flow cytometry systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem*. January; 49(pt 1):17-28; Linden, et. al., *Semin Throm Hemost*. 2004 October; 30(5):502-11; Alison, et al. *J Pathol*, 2010 December; 222(4):335-344; and Herbig, et al. (2007) *Crit Rev Ther Drug Carrier Syst*. 24(3):203-255; the disclosures of which are incorporated herein by reference. In certain instances, flow cytometry systems of interest include BD Biosciences FACSCanto™ flow cytometer, BD Biosciences FACSVantage™, BD Biosciences FACSort™, BD Biosciences FACSCount™, BD Biosciences FACScan™, and BD Biosciences FACSCalibur™ systems, a BD Biosciences Influx™ cell sorter, BD Biosciences Jazz™ cell sorter and BD Biosciences Aria™ cell sorter or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

Methods for Measuring Light Collected from an Irradiated Sample

Aspects of the disclosure also include methods for measuring light from a sample (e.g., in the flow stream in a flow cytometer). In practicing methods according to embodiments, a sample is irradiated with a light source and light from the sample is detected with the light detection systems having two or more photodetector arrays as described above. In some embodiments, the sample is a biological sample. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

In practicing the subject methods, a sample (e.g., in a flow stream of a flow cytometer) is irradiated with light from a light source. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Where methods include irradiating with a broadband light source, broadband light source protocols of interest may include, but are not limited to, a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, methods includes irradiating with a narrow band light source emitting a particular wavelength or a narrow range of wavelengths, such as for example with a light source which emits light in a narrow range of wavelengths like a range of 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Where methods include irradiating with a narrow band light source, narrow band light source protocols of interest may include, but are not limited to, a narrow wavelength LED, laser diode or a broadband light source coupled to one or more optical bandpass filters, diffraction gratings, monochromators or any combination thereof.

In certain embodiments, methods include irradiating the sample with one or more lasers. As discussed above, the type and number of lasers will vary depending on the sample as well as desired light collected and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the methods include irradiating the flow stream with a dye laser, such as a stilbene, coumarin or rhodamine laser. In yet other instances, methods include irradiating the flow stream with a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, methods include irradiating the flow stream with a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium$_2$O$_3$ laser or cerium doped lasers and combinations thereof.

The sample may be irradiated with one or more of the above mentioned light sources, such as 2 or more light sources, such as 3 or more light sources, such as 4 or more light sources, such as 5 or more light sources and including 10 or more light sources. The light source may include any combination of types of light sources. For example, in some embodiments, the methods include irradiating the sample in the flow stream with an array of lasers, such as an array having one or more gas lasers, one or more dye lasers and one or more solid-state lasers.

The sample may be irradiated with wavelengths ranging from 200 nm to 1500 nm, such as from 250 nm to 1250 nm, such as from 300 nm to 1000 nm, such as from 350 nm to 900 nm and including from 400 nm to 800 nm. For example, where the light source is a broadband light source, the sample may be irradiated with wavelengths from 200 nm to 900 nm. In other instances, where the light source includes a plurality of narrow band light sources, the sample may be irradiated with specific wavelengths in the range from 200 nm to 900 nm. For example, the light source may be plurality of narrow band LEDs (1 nm-25 nm) each independently emitting light having a range of wavelengths between 200 nm to 900 nm. In other embodiments, the narrow band light source includes one or more lasers (such as a laser array) and the sample is irradiated with specific wavelengths ranging from 200 nm to 700 nm, such as with a laser array having gas lasers, excimer lasers, dye lasers, metal vapor lasers and solid-state laser as described above.

Where more than one light source is employed, the sample may be irradiated with the light sources simultaneously or sequentially, or a combination thereof. For example, the sample may be simultaneously irradiated with each of the light sources. In other embodiments, the flow stream is sequentially irradiated with each of the light sources. Where more than one light source is employed to irradiate the sample sequentially, the time each light source irradiates the sample may independently be 0.001 microseconds or more, such as 0.01 microseconds or more, such as 0.1 microseconds or more, such as 1 microsecond or more, such as 5 microseconds or more, such as 10 microseconds or more, such as 30 microseconds or more and including 60 microseconds or more. For example, methods may include irradiating the sample with the light source (e.g. laser) for a duration which ranges from 0.001 microseconds to 100 microseconds, such as from 0.01 microseconds to 75 microseconds, such as from 0.1 microseconds to 50 microseconds, such as from 1 microsecond to 25 microseconds and including from 5 microseconds to 10 microseconds. In embodiments where sample is sequentially irradiated with two or more light sources, the duration sample is irradiated by each light source may be the same or different.

The time period between irradiation by each light source may also vary, as desired, being separated independently by a delay of 0.001 microseconds or more, such as 0.01 microseconds or more, such as 0.1 microseconds or more, such as 1 microsecond or more, such as 5 microseconds or more, such as by 10 microseconds or more, such as by 15 microseconds or more, such as by 30 microseconds or more and including by 60 microseconds or more. For example, the time period between irradiation by each light source may range from 0.001 microseconds to 60 microseconds, such as from 0.01 microseconds to 50 microseconds, such as from 0.1 microseconds to 35 microseconds, such as from 1 microsecond to 25 microseconds and including from 5 microseconds to 10 microseconds. In certain embodiments, the time period between irradiation by each light source is 10 microseconds. In embodiments where sample is sequentially irradiated by more than two (i.e., 3 or more) light sources, the delay between irradiation by each light source may be the same or different.

The sample may be irradiated continuously or in discrete intervals. In some instances, methods include irradiating the sample in the sample with the light source continuously. In other instances, the sample in is irradiated with the light source in discrete intervals, such as irradiating every 0.001 millisecond, every 0.01 millisecond, every 0.1 millisecond, every 1 millisecond, every 10 milliseconds, every 100 milliseconds and including every 1000 milliseconds, or some other interval.

Depending on the light source, the sample may be irradiated from a distance which varies such as 0.01 mm or more, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more. Also, the angle or irradiation may also vary, ranging from 10° to 90°, such as from 15° to 85°, such as from 20° to 80°, such as from 25° to 75° and including from 30° to 60°, for example at a 90° angle.

As discussed above, in embodiments light from the irradiated sample is conveyed to a light detection system as described herein and measured by one or more photodetectors. In practicing the subject methods, light is propagated to the first photodetector array in the light detection system. The light is further propagated to each additional photodetector array through an optical adjustment component positioned in an optical path between the photodetector arrays. Light is directed to each photodetector in the photodetector arrays which measures the collected light at one or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring the collected light at 400 or more different wavelengths.

In some embodiments, methods include measuring the collected light over a range of wavelengths (e.g., 200 nm-1000 nm). For example, methods may include collecting spectra of light over one or more of the wavelength ranges of 200 nm-1000 nm. In yet other embodiments, methods include measuring collected light at one or more specific wavelengths. For example, the collected light may be measured at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, methods including measuring wavelengths of light which correspond to the fluorescence peak wavelength of certain fluorophores.

The collected light may be measured continuously or in discrete intervals. In some instances, methods include taking measurements of the light continuously. In other instances, the light is measured in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

Measurements of the collected light may be taken one or more times during the subject methods, such as 2 or more times, such as 3 or more times, such as 5 or more times and including 10 or more times. In certain embodiments, the light propagation is measured 2 or more times, with the data in certain instances being averaged.

In some embodiments, methods include adjusting the light before detecting the light with the subject light detection systems. For example, the light from the sample source may be passed through one or more lenses, mirrors, pinholes, slits, gratings, light refractors, and any combination thereof. In some instances, the collected light is passed through one or more focusing lenses, such as to reduce the profile of the light directed to the light detection system or optical collection system as described above. In other instances, the emitted light from the sample is passed through one or more collimators to reduce light beam divergence conveyed to the light detection system.

Kits

Aspects of the invention further include kits, where kits include two or more photodetector arrays, each photodetector array having two or more photodetectors and optical adjustment components (e.g., beam splitter, collimating lenses, mirrors, wavelength separators, pinholes, etc.) for positioning in an optical path between each photodetector array. Kits may also include an optical collection component, such as fiber optics (e.g., fiber optics relay bundle) or components for a free-space relay system. In some instances, kits further include one or more photodetectors, such as photomultiplier tubes (e.g., metal package photomultiplier tubes).

In some embodiments, kits include 2 or more of the components of the light detection systems disclosed herein, such as 3 or more and including 5 or more. In some instances, the kits can include one or more assay components (e.g., labeled reagents, buffers, etc., such as described above). In some instances, the kits may further include a sample collection device, e.g., a lance or needle configured to prick skin to obtain a whole blood sample, a pipette, etc., as desired.

The various assay components of the kits may be present in separate containers, or some or all of them may be pre-combined. For example, in some instances, one or more components of the kit, e.g., the connectors, orifice plates are present in a sealed pouch, e.g., a sterile foil pouch or envelope.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

The subject light detection systems find use where the characterization of a sample by optical properties, in particular where low levels of light are collected, is desired. In some embodiments, the systems and methods described herein find use in flow cytometry characterization of biological samples labelled with fluorescent tags. In other embodiments, the systems and methods find use in spectroscopy of transmitted or scattered light. In addition, the subject systems and methods find use in increasing the obtainable signal from light collected from a sample (e.g., in a flow stream). In certain instances, the present disclosure finds use in enhancing measurement of light collected from a sample that is irradiated in a flow stream in a flow cytometer. Embodiments of the present disclosure find use where enhancing the effectiveness of emission measurements in flow cytometry are desired, such as in research and high throughput laboratory testing. The present disclosure also finds use where it is desirable to provide a flow cytometer with improved cell sorting accuracy, enhanced particle collection, reduced energy consumption, particle charging efficiency, more accurate particle charging and enhanced particle deflection during cell sorting.

The present disclosure also finds use in applications where cells prepared from a biological sample may be desired for research, laboratory testing or for use in therapy. In some embodiments, the subject methods and devices may facilitate the obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems facilitate obtaining cells from fluidic or tissue samples to be used in therapy. Methods and devices of the present disclosure allow for separating and collecting cells from a biological sample (e.g., organ, tissue, tissue fragment, fluid) with enhanced efficiency and low cost as compared to traditional flow cytometry systems.

Notwithstanding the appended clauses, the disclosure set forth herein is also defined by the following clauses:

1. A light detection system comprising:
   a first photodetector array in optical communication with a second photodetector array, wherein the first photodetector array and second photodetector array each comprise two or more photodetectors; and
   an optical adjustment component positioned in an optical path between the first photodetector array and the second photodetector array.

2. The light detection system according to clause 1, wherein the optical adjustment component comprises a collimator that collimates light between the first photodetector array and the second photodetector array.

3. The light detection system according to any one of clauses 1-2, wherein the optical adjustment component comprises a beam splitter.

4. The light detection system according to any one of clauses 1-3, wherein the optical adjustment component comprises a wavelength separator.

5. The light detection system according to any one of clauses 1-4, wherein the optical adjustment component comprises a dichroic mirror.

6. The light detection system according to any one of clauses 1-5, wherein two or more optical adjustment components are positioned between the first photodetector array and the second photodetector array.

7. The light detection system according to clause 6, wherein optical adjustment component comprises a dichroic mirror and a collimator.

8. The light detection system according to any one of clauses 1-7, wherein a dichroic mirror is positioned adjacent to one or more photodetectors in each photodetector array.

9. The light detection system according to any one of clauses 1-8, wherein the system further comprises:
   a third photodetector array; and
   an optical adjustment component positioned in an optical path between the second photodetector array and the third photodetector array.

10. The light detection system according to clause 9, wherein the optical adjustment component comprises a collimator.

11. The light detection system according to any one of clauses 9-10, wherein the optical adjustment component comprises a dichroic mirror.

12. The light detection system according to any one of clauses 1-11, wherein the system comprises 10 or more photodetector arrays.

13. The light detection system according to any one of clauses 1-11, wherein the photodetector arrays are positioned along a single axis.

14. The light detection system according to any one of clauses 1-11, wherein the photodetector arrays are positioned along more than one axis.

15. The light detection system according to any one of clauses 1-11, wherein the photodetector arrays are positioned along two or more parallel axes.

16. The light detection system according to any one of clauses 1-11, wherein the photodetector arrays have a polygonal configuration in the light detection system.

17. The light detection system according to clause 16, wherein the photodetector arrays have a heptagonal configuration or octagonal configuration.

18. The light detection system according to any one of clauses 1-17, wherein each photodetector array comprises an aligner for aligning two or more photodetector arrays.

19. The light detection system according to any one of clauses 1-18, wherein each photodetector array comprises a connector for coupling two or more photodetector arrays.

20. The light detection system according to any one of clauses 1-19, wherein the light detection system comprises a proximal end and a distal end, wherein:
   the proximal end comprises an orifice for receiving light; and
   the distal end comprises a beam stop.

21. The light detection system according to any one of clauses 1-20, where the photodetectors are photomultiplier tubes.

22. The light detection system according to clause 21, wherein the photomultiplier tube is a metal package photomultiplier tube.

23. A system comprising:
   a light source; and
   a light detection system comprising:
   a first photodetector array in optical communication with a second photodetector array, wherein the first photodetector array and second photodetector array each comprise two or more photodetectors; and
   an optical adjustment component positioned in an optical path between the first photodetector array and the second photodetector array.

24. The system according to clause 23, wherein the light source is a laser.

25. The system according to any one of clauses 23-24, wherein the system is a flow cytometer.

26. The system according to any one of clauses 23-25, further comprising an optical collection system for propagating light to the light detection system.

27. The system according to clause 26, wherein the optical collection component comprises fiber optics.

28. The system according to clause 27, wherein the optical collection component is a fiber optics light relay bundle.

29. The system according to clause 27, wherein the optical collection component is a free-space light relay system.

30. The system according to any one of clauses 23-29, wherein the optical adjustment component comprises a collimator that collimates light between the first photodetector array and the second photodetector array.

31. The system according to any one of clauses 23-30, wherein the optical adjustment component comprises a beam splitter.

32. The system according to any one of clauses 23-31, wherein the optical adjustment component comprises a dichroic mirror.

33. The system according to any one of clauses 23-32, wherein the optical adjustment component comprises a wavelength separator.
34. The system according to any one of clauses 23-33, wherein two or more optical adjustment components are positioned between the first photodetector array and the second photodetector array.
35. The system according to clause 34, wherein optical adjustment component comprises a dichroic mirror and a collimator.
36. The system according to any one of clauses 23-35, wherein a dichroic mirror is positioned adjacent to one or more photodetectors in each photodetector array.
37. The system according to any one of clauses 23-36, wherein the light detection system further comprises:
   a third photodetector array; and
   an optical adjustment component positioned in an optical path between the second photodetector array and the third photodetector array.
38. The system according to clause 37, wherein the optical adjustment component comprises a collimator.
39. The system according to any one of clauses 36-38, wherein the optical adjustment component comprises a dichroic mirror.
40. The system according to any one of clauses 23-39, wherein the light detection system comprises 10 or more photodetector arrays.
41. The system according to any one of clauses 23-40, wherein the photodetector arrays are positioned along a single axis.
42. The system according to any one of clauses 23-41, wherein the photodetector arrays are positioned along more than one axis.
43. The system according to any one of clauses 23-42, wherein the photodetector arrays are positioned along two or more parallel axes.
44. The system according to any one of clauses 23-42, wherein the photodetector arrays have a polygonal configuration in the light detection system.
45. The system according to clause 44, wherein the photodetector arrays have a heptagonal configuration or octagonal configuration.
46. The system according to any one of clauses 23-45, wherein each photodetector array comprises an aligner for aligning two or more photodetector arrays.
47. The system according to any one of clauses 23-46, wherein each photodetector array comprises a connector for coupling two or more photodetector arrays.
48. The system according to any one of clauses 23-46, wherein the light detection system comprises a proximal end and a distal end, wherein:
   the proximal end comprises an orifice for receiving light propagated from a sample irradiated by the light source; and
   the distal end comprises a beam stop.
49. The system according to any one of clauses 23-48, where the photodetectors are photomultiplier tubes.
50. The system according to clause 49, wherein the photomultiplier tube is a metal package photomultiplier tube.
51. A method comprising:
   detecting light from the flow stream with a light detection system comprising:
   a first photodetector array in optical communication with a second photodetector array, wherein the first photodetector array and second photodetector array each comprise two or more photodetectors; and
   an optical adjustment component positioned in an optical path between the first photodetector array and the second photodetector array.
52. The method according to clause 51, further comprising irradiating a sample in a flow stream in an interrogation field with a light source.
53. The method according to any one of clauses 51-52, wherein the flow stream is irradiated with a light source at a wavelength from 200 nm to 800 nm.
54. The method according to any one of clauses 52-53, wherein the light source is a laser.
55. The method according to any one of clauses 52-54, wherein light from the flow stream is propagated to the light detection system with an optical collection component.
56. The method according to clause 55, wherein the optical collection component comprises fiber optics.
57. The method according to clause 56, wherein the optical collection component comprises a fiber optics light relay bundle.
58. The method according to clause 55, wherein the optical collection component comprises a free-space light relay system.
59. The method according to clause 51, further comprising measuring the detected light at one or more wavelengths.
60. A kit comprising:
   two or more photodetector arrays, each photodetector array comprising two or more photodetectors; and
   an optical adjustment component configured for positioning in an optical path between each photodetector array.
61. The kit according to clause 60, wherein the optical adjustment component comprises a collimator.
62. The kit according to any one of clauses 60-61, wherein the optical adjustment component comprises a beam splitter.
63. The kit according to any one of clauses 60-62, wherein the optical adjustment component comprises a dichroic mirror.
64. The kit according to any one of clauses 60-63, wherein the photodetectors are photomultiplier tubes.
65. The kit according to any one of clauses 60-64, wherein the photomultiplier tube is a metal package photomultiplier tube.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A light detection system comprising:
a first photodetector array comprising:
a first photodetector and a second photodetector; and
a first optical adjustment component configured to propagate light directly from the first photodetector to the second photodetector;
a second photodetector array comprising:
a third photodetector and a fourth photodetector; and
a second optical adjustment component configured to propagate light directly from the third photodetector to the fourth photodetector; and
a third optical adjustment component positioned in an optical path between the first photodetector array and the second photodetector array, wherein the optical adjustment component is configured to propagate light from the first photodetector array to the second photodetector array.

2. The light detection system according to claim 1, wherein the third optical adjustment component comprises a collimator that collimates light between the first photodetector array and the second photodetector array.

3. The light detection system according to claim 1, wherein the third optical adjustment component comprises a beam splitter.

4. The light detection system according to claim 1, wherein the third optical adjustment component comprises a wavelength separator.

5. The light detection system according to claim 1, wherein the third optical adjustment component comprises a dichroic mirror.

6. The light detection system according to claim 1, wherein two or more optical adjustment components are positioned between the first photodetector array and the second photodetector array.

7. The light detection system according to claim 6, wherein the two or more optical adjustment components positioned between the first photodetector array and the second photodetector array comprises a dichroic mirror and a collimator.

8. The light detection system according to claim 1, wherein the first optical adjustment component comprises a dichroic mirror positioned adjacent to the first photodetector in the first photodetector array.

9. The light detection system according to claim 1, wherein the system further comprises:
a third photodetector array; and
a fourth optical adjustment component positioned in an optical path between the second photodetector array and the third photodetector array, wherein the fourth optical adjustment component is configured to propagate light from the second photodetector array to the third photodetector array.

10. The light detection system according to claim 9, wherein the fourth optical adjustment component comprises a collimator.

11. The light detection system according to claim 9, wherein the fourth optical adjustment component comprises a dichroic mirror.

12. The light detection system according to claim 1, wherein the system comprises 10 or more photodetector arrays.

13. The light detection system according to claim 1, wherein the photodetector arrays have a polygonal configuration in the light detection system.

14. The light detection system according to claim 13, wherein the photodetector arrays have a heptagonal configuration or octagonal configuration.

15. The light detection system according to claim 1, wherein each photodetector array comprises an aligner for aligning two or more photodetector arrays.

16. The light detection system according to claim 1, wherein each photodetector array comprises a connector for coupling two or more photodetector arrays.

17. The light detection system according to claim 1, wherein the light detection system comprises a proximal end and a distal end, wherein:
the proximal end comprises an orifice for receiving light; and
the distal end comprises a beam stop.

18. A system comprising:
a light source; and
a light detection system comprising:
a first photodetector array comprising:
a first photodetector and a second photodetector; and
a first optical adjustment component configured to propagate light directly from the first photodetector to the second photodetector;
a second photodetector array comprising:
a third photodetector and a fourth photodetector; and
a second optical adjustment component configured to propagate light directly from the third photodetector to the fourth photodetector; and
a third optical adjustment component positioned in an optical path between the first photodetector array and the second photodetector array, wherein the optical adjustment component is configured to propagate light from the first photodetector array to the second photodetector array.

19. The system according to claim 18, wherein the system is a flow cytometer.

20. A method comprising:
detecting light from the flow stream with a light detection system comprising:
a first photodetector array comprising:
a first photodetector and a second photodetector; and
a first optical adjustment component configured to propagate light directly from the first photodetector to the second photodetector;
a second photodetector array comprising:
a third photodetector and a fourth photodetector; and
a second optical adjustment component configured to propagate light directly from the third photodetector to the fourth photodetector; and
a third optical adjustment component positioned in an optical path between the first photodetector array and the second photodetector array, wherein the optical adjustment component is configured to propagate light from the first photodetector array to the second photodetector array.

* * * * *